United States Patent
Gordon

(12) 
(10) Patent No.: US 6,447,763 B1
(45) Date of Patent: *Sep. 10, 2002

(54) METHOD AND SYSTEM FOR PRODUCTION AND COLLECTION OF LAVAGE INDUCED STOOL (LIS) FOR CHEMICAL AND BIOLOGIC TESTS OF CELLS

(76) Inventor: Ian L. Gordon, 6361 Deborah St., Long Beach, CA (US) 90815

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/097,098

(22) Filed: Jun. 12, 1998

(51) Int. Cl.[7] .............................................. A61K 31/74
(52) U.S. Cl. .................................... 424/78.01; 514/892
(58) Field of Search ............................ 435/4; 424/439, 424/78.01; 514/892

(56) References Cited

U.S. PATENT DOCUMENTS

| | | |
|---|---|---|
| 4,101,279 A | 7/1978 | Aslam .......................... 422/99 |
| 4,190,059 A | 2/1980 | Holt ............................ 600/563 |
| 4,309,782 A | 1/1982 | Paulin ........................... 4/661 |
| 4,525,156 A | 6/1985 | Benusa et al. ................. 604/28 |
| 4,683,197 A | 7/1987 | Gallati ....................... 435/7.91 |
| 4,709,705 A | 12/1987 | Truglio ........................ 600/563 |
| 4,773,430 A | 9/1988 | Porath ......................... 600/581 |
| 4,975,286 A | * 12/1990 | Hechter ....................... 424/682 |

(List continued on next page.)

FOREIGN PATENT DOCUMENTS

EP 0771562 * 5/1997

OTHER PUBLICATIONS

Goerg et al., Naunyn–Schmiedeberg's Arch Pharmacol 312(1): 91–98 (1980). Abstract.*
Cline et al., J. Clin. Invest. 58(2): 380–390 (1976).*
Bretagne et al., GUT 22(4): 264–269 (Apr. 1981).*
Foord, Clinical Radiology 33(4): 467–469 (Jul. 1982).*
Gordon, I.L. et al., Cancer, vol. 68(1), p. 106–110, 1991.*
Tomlinson, T.L. et al., AJR, vol. 151, p. 947–950, Nov. 1988.*
Girard, C.M. et al., AJR, vol. 142, p. 1147–1149, Jun. 1984.*
Beck, D.E. et al., Arch Surg., vol. 126(5), p. 552–555, May 1991.*
Morotomi, M. et al., Applied & Environ. Microbiol., vol. 55(4), p. 1026–1028, Apr. 1989.*
"Bisacodyl"—downloaded from the Internet on Oct. 7, 1998. Excerpt from the Complete Guide to Prescription & Non-Prescription Drugs by H. Winter Griffith. The Putnam Berkley Group, 1996.*
Handy, L.M. et al., Scandanavian J. of Gastroenterology, vol. 31(7), p. 700–705, 1996.*

Gordon et al., "Increased Exfoliation of Gut Mucosal Cells Induced by Chenodeoxycholic Acid" Gastroenterology 106(4Suppl):a387, 1994.
Paul Rozen, et al., Exfoliative Colonic Cytology, Acta Cytologica, Sep.–Oct. 1990, vol. 34, No. 5, pp. 627–631, The International Academy of Cytology.
Genevieve M. Bader, et al., The Application of Cytology in The Diagnosis of Cancer of the Rectum, Sigmoid, and Descending Colon, Cancer, Mar. 1952, vol. 5, pp. 307–314.
S. Gupta, et al., Simple Gastric Lavage Cytology in Carcinoma Stomach; Its Relevance To Developing Countries, Tropical and Geographical Medicine, Oct. 21, 1997, pp. 483–486.
Marshall S. Bedine, et al., A comparison of washing and brushing cytology and biopsy in the diagnosis of malignant disease of the esophagus, stomach, and colon, Gastrointestinal Endoscopy, vol. 19, No. 2, 1972; Howard F. Raskin, et al., Exfoliative Cytology in Diagnosis of Cancer of the Colon, Exfoliative Cytology, pp. 46–57.
M. J. Oakland, The Diagnosis of Carcinoma of the Colon by Exfoliatvie Cytology, Proceeding of the Royal Society of Medicine, 1964, 57: 279–282.
Dwight F. Miller, et al., An Evaluation of A Simplified Technique for Colonic Exfoliative Cytology, Acta Cytollgical, 1969, vol. 13, pp. 53–56.
Bader, G.M. et al. The Application of Cytology in the Diagnosis of Cancer of the Rectum, Sigmoid and Descending Colon. Cancer. Mar. 1952, vol. 5, No. 2, pp. 307–314.
Gordon, I.L. et al. Cytologic Detection of Colorectal Cancer After Administration of Oral Lavage Solution. Cancer (Phila.). 1991, vol. 68, No. 1, pp. 106–110.
Oakland, D.J. The Diagnosis of Carcinoma of the Colon by Exfoliative Cytology. Proceedings of the Royal Society of Medicine. 1964, vol. 57, pp. 279–282.
Rozen, M.B. et al. Exfoliative Colonic Cytology: A Simplified Method of Collection and Intitial Results. Acta Cytoligica. Sep.–Oct. 1990, vol. 34, No. 5, pp. 627–631.

*Primary Examiner*—Jean C. Witz
(74) *Attorney, Agent, or Firm*—O'Melveny & Myers LLP

(57) ABSTRACT

Beverages are provided and administered for producing LIS samples containing cells exfoliated from throughout the gut in sufficient numbers and free of interfering substances such as formed fecal particles for chemical assays and biologic assays for nucleic acid sequence information, and medical diagnosis. A kit is also provided for use by patients without assistance to produce a LIS sample suitable for analysis. A collection kit employs a sequence of the beverages and other ingested substances to produce preserved cells for medical diagnosis, allowing cytologic analysis of the LIS for diagnosis of foregut and hindgut disease. A preliminary cathartic lavage is used to cleanse a patient's digestive tract; at least one stool induced by the preliminary cathartic lavage is collected; and a final cathartic lavage is used to exfoliate and preserve cells from a patient's digestive tract. Time release capsules containing a cathartic medicament can also be used after completing preliminary lavage administration. The kit also allows provides apparatus for collection, sealing, and packing of the collected LIS specimen for analysis.

10 Claims, 1 Drawing Sheet

U.S. PATENT DOCUMENTS

| | | | |
|---|---|---|---|
| 5,064,766 A | | 11/1991 | Wardlaw et al. ............... 436/66 |
| 5,077,048 A | * | 12/1991 | Kimura et al. ............... 424/422 |
| 5,124,144 A | | 6/1992 | Giorgetti et al. ......... 424/78.01 |
| 5,219,573 A | * | 6/1993 | Tarka, Jr. et al. ............ 424/439 |
| 5,380,647 A | | 1/1995 | Bahar |
| 5,416,025 A | | 5/1995 | Krepinsky et al. |
| 5,460,969 A | | 10/1995 | Fielder et al. |
| 5,616,346 A | * | 4/1997 | Aronchick .................. 424/606 |

* cited by examiner

METHOD AND SYSTEM FOR PRODUCTION AND COLLECTION OF LAVAGE INDUCED STOOL (LIS) FOR CHEMICAL AND BIOLOGIC TESTS OF CELLS

BACKGROUND OF THE INVENTION

1. Field of the Invention

This invention relates generally to screening tests for gastrointestinal disease, and more particularly concerns a method and system for enhancing yield and improving patient comfort in production and collection of exfoliated cells from the gastrointestinal tract of a patient for chemical and biologic testing.

2. Description of Related Art

Standard testing procedures for cancer of the gut commonly entail either direct endoscopic visualization of the hollow viscera through which food passes in sequence, i.e., the pharynx, esophagus, stomach, small intestines, large intestine, and rectum, or contrast x-ray visualization of the lumen for abnormalities in the wall of the gut.

Screening tests are also known for detecting chemical markers, such as hemoglobin, ras DNA oncogenes and carcinoembryonic antigen (CEA), each of which is independently associated with gastrointestinal cancer. These screening tests typically involve either collecting formed feces and applying a sample of the collected stool to a test medium containing an indicator for the presence of the chemical marker associated with gastrointestinal cancer, or administering a laxative purge to the patient, collecting a watery fecal sample, and applying the watery fecal sample to a test medium containing an indicator. Typically when a laxative purge is employed, either the first or second watery post-purge bowel movement is collected following administration of the purge. However, conventional tests for chemical markers are commonly subject to false negatives and/or false positives, which can severely interfere with proper diagnosis and care for a patient.

It is thus apparent that there is a need for a test that is more reliable than chemical marker screening. It would be desirable to provide a screening method and system based on analysis of cells exfoliated from the tissues lining the gut. Conventionally, recovery of material from the gut suitable for cellular analysis was performed with either enemas or surgical methods requiring tubes or endoscopes to be passed into the area being investigated, which are invasive, uncomfortable for the patient, and expensive. Analysis of spontaneously passed stools for cellular parameters such as morphology or nucleic acid sequences is limited by the conditions existing in the gut, which cause rapid destruction of exfoliated cells, and conventional techniques do not adequately provide cells that are sufficiently preserved to be useful for cell based analysis.

It has been demonstrated that malignant cells can be reliably detected in bowel movements induced by oral administration of a balanced electrolyte lavage solution containing polyethylene glycol. The cells collected from the induced bowel movements were stained according to standard methods, and malignant cells were identified in the stained preparations in all patients with cancer. However, it was found that specimens were stable for only a few hours, with prolonged storage prior to processing damaging diagnostic accuracy, and that the test procedure could only detect colorectal cancer. In addition, processing of samples required trained technicians, with fixation and filtration procedures being required in the laboratory after specimen transport.

There is thus a need for a method and system for producing and collecting lavage induced stool (LIS) samples containing cells exfoliated from throughout the gut in sufficient numbers and free of interfering substances such as formed fecal particles for chemical assays and biologic assays for nucleic acid sequence information, for medical diagnosis of cancer of the colon, rectum, stomach and esophagus and other medical conditions using standard cytopathology methods. It would also be desirable to provide a method for producing and collecting LIS samples containing higher numbers of exfoliated cells, and with improved preservation of morphological and chemical properties than has been achievable in the prior art. It would be desirable to provide a kit for carrying out the method of the invention, for use by patients without assistance to produce a LIS sample suitable for analysis. It would also be desirable to provide a collection kit that employs a sequence of ingested substances to produce preserved cells for medical diagnosis, allowing cytologic analysis of the LIS for diagnosis of foregut and hindgut disease, and providing better palatability and comfort for patients than previous lavage stool cytology methods. The present invention meets these needs.

SUMMARY OF THE INVENTION

Briefly, and in general terms, the present invention provides for a method for producing LIS samples containing cells exfoliated from throughout the gut in sufficient numbers and free of interfering substances such as formed fecal particles for chemical assays and biologic assays for nucleic acid sequence information, and medical diagnosis. From such LIS samples, cancer of the colon, rectum, stomach and esophagus and other medical conditions can be readily diagnosed using standard cytopathology methods. The method allows analysis of cells exfoliated from throughout the gastrointestinal tract, and produces samples with higher numbers of cells with better preservation of morphological and chemical properties than has been achievable heretofore. The method of the invention is also useful for mechanical cleansing of the gut and bowel compatible for preparation of patients for surgical procedures such as fiberoptic endoscopy.

The invention also provides for a kit for use by patients without assistance to produce a LIS sample suitable for analysis. The collection kit of the invention employs a sequence of ingested substances to produce preserved cells for medical diagnosis, allowing cytologic analysis of the LIS for diagnosis of foregut and hindgut disease. Home collection and the use of fixatives make the test kit convenient and the cost of the overall test procedure relatively low. Compared to stool produced by ingestion of PEG lavage solution, stools produced by the kit procedure have more and purer exfoliated cells improving diagnostic accuracy. The specific sequence of substances administered and kit procedures provide better palatability and comfort than previous lavage stool cytology methods. The kit permits the low cost, non-invasive, and accurate detection of common gastrointestinal malignancies. The kit allows a subject to perform the collection procedure at home safely, conveniently, and with greater comfort. The preserved specimen can be stored several days without damaging its diagnostic potential, and can be safely transported by carrier or post. Home administration and prolonged specimen stability greatly increase the practicality and cost effectiveness of the test procedure. The combination of ingested substances leads to improved purity and yield of exfoliated cells, and allows better diagnosis of disease of the stomach and esophagus, in addition to allowing detection of colorectal conditions.

The invention accordingly provides for a method for producing and collecting lavage induced stools for chemical and biological tests of cells exfoliated from a patient's digestive tract. The steps of the method generally comprise orally administering a preliminary cathartic lavage to cleanse a patient's digestive tract; collecting at least one stool induced by the preliminary cathartic lavage; and administering a final cathartic lavage to exfoliate and preserve cells from a patient's digestive tract. In one currently preferred embodiment, the step of orally administering a preliminary cathartic lavage comprises orally administering approximately 500 ml of a mannitol solution and collecting the patient's stool, and repeating this step until the patient's stool is substantially free of sediment or formed stool particles. In another currently preferred aspect of the invention, the step of orally administering a preliminary cathartic lavage can further comprise orally administering at least one timed release capsule containing medication that increases exfoliation of cells from the lining of the gut after completing preliminary lavage administration, and waiting a predetermined time interval, such as approximately two hours, before the next step. This preliminary phase can additionally also comprise collecting a first solid stool and a second liquid stool for further analysis. The patient is allowed an electrolyte beverage ad lib during this stage until feces collection is finished. In a currently preferred embodiment, the step of administering a final cathartic lavage comprises administering approximately 250 mls of a final lavage solution every 15 minutes until a the patient's stool is substantially clear. The method of the invention can also comprise the step of processing of the collected LIS specimen for return for analysis, and generally comprises transferring approximately 50 to 100 ml of the LIS specimen collected in a toilet pan into a filtration apparatus. The LIS specimen is then transferred via the filtration apparatus into a specimen container having a fixative for preserving the LIS specimen. After the specimen container is filled to a predetermined level, the safety lid is secured and the sealed container is placed in a mailing carton meeting U.S. biohazard regulations for transport via courier or post to a laboratory for analysis.

The invention thus also provides for a specimen container and filter device that are specially designed to promote safe and convenient processing of the sample, with a special seal inside the specimen container to prevent splashing or leakage of fixative during the transfer from the filter device.

In another aspect, the invention provides for a test kit for producing and collecting lavage induced stool for chemical and biological tests of cells exfoliated from a patient's digestive tract. The invention is a kit to be used at home for collection of a stool sample induced by the ingestion of a sequence of beverages, medication and medicated foods. The kit components and procedures produce stool specimens with preserved exfoliated gastrointestinal cells suitable for medical diagnosis based on histopathologic, biologic, and chemical tests. Cells produced from the kit procedures and components are derived from both the foregut and hindgut allowing diagnosis of both esophageal and rectal cancer as well as other diseases. The kit components and procedures are designed to make the ingested substances palatable and the collection of stool samples convenient and safe.

The test kit can comprise instructional materials including color pictures of LIS samples in collection containers for comparison with collected samples while carrying out the method of the invention; disposable collection apparatus, such as beverage containers, collection pans that fit standard toilet bowl dimensions, collection syringes, a filtration device, and a LIS specimen container with fixative (such as 10% buffered formalin, for example) to collect solid and liquid bowel motions generated by the test procedure, as well as a mailing carton, labels and gloves.

The test kit of the invention also preferably contains an advanced formulation of a beverage or beverages and/or powdered chemicals for reconstitution as beverages or medication, medications, foods, and medicated foods. In one preferred aspect of the kit, the powdered chemicals include sufficient powder to prepare approximately 6 liters of a sweet tasting balanced electrolyte and salt solution similar to sports drinks such as Gatorade, by reconstitution with water. The drink may be modified with additives such as hormones, proteolytic enzymes, calcium chelating agents such as EDTA, mucolytics, bile salts such as chenodeoxycholate, and buffers such as bicarbonate salts and/or HEPES, which induce increased exfoliation and/or preservation of cells. In another preferred aspect of the invention, the kit can also include hard candies based on sorbitol and/or dextrose, to ameliorate the flavor of a final lavage solution. These candies may contain EDTA or other drugs which promote exfoliation of gut mucosa cells. The kit also includes a cathartic medication, such as 250 ml of magnesium citrate, to induce the production of a formed stool. The kit further includes sufficient powder to prepare up to one liter of a preliminary lavage solution, and may, for example, contain buffered mannitol. The preliminary lavage solution may also contain additives such as hormones, proteolytic enzymes, calcium chelating agents such as EDTA, mucolytics, bile salts such as chenodeoxycholate, and buffers such as bicarbonate salts and/or HEPES, to induce increased exfoliation and/or preservation of cells. The kit further contains sufficient powder to prepare up to 4 liters of a final lavage solution containing buffers, inorganic salts, polyethylene glycol, and additives such as hormones, proteolytic enzymes, calcium chelating agents such as EDTA, mucolytics, bile salts such as chenodeoxycholate, and buffers such as bicarbonate salts and/or HEPES, to induce increased exfoliation and/or preservation of cells. The kit may additionally contain time release capsules containing substances such as hormones, drugs, buffer salts, proteases, EDTA, or bile salts, which when released into the gut at the proper time in the test procedure improve the yield or preservation of cells recovered in the LIS.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
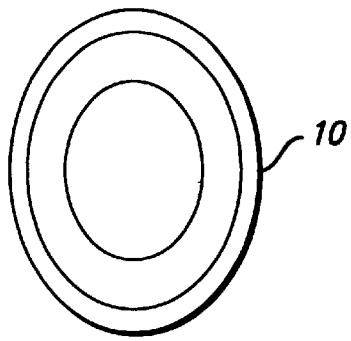
FIG. 1 is a top plan view of a toilet pan for use in the method and test kit of according to the invention for producing and collecting lavage induced stools for chemical and biological tests of cells exfoliated from a patient's digestive tract.

Standard testing procedures for cancer of the gastrointestinal tract can be invasive, uncomfortable for the patient, and expensive, and can be subject to false negatives and/or false positives. Conditions normally existing in the gastrointestinal tract can also cause rapid destruction of markers and exfoliated cells, which can make conventional tests based upon them unreliable. Specimens collected may also be stable for short periods of time, and of limited value. In addition, conventional sampling procedures commonly require trained technicians.

Lavage solutions based on polyethylene glycol currently used in clinical practice typically produce a watery diarrhea containing exfoliated cells. Analysis of the cells present in such LIS samples from patients with gastrointestinal malignancy and normal patients indicate that diagnostic tests are capable of identifying malignancies, and that such LIS samples may contain malignant cells from areas of the upper gut as well, such as the esophagus and stomach, allowing for testing for malignancy throughout the entire gut by LIS techniques. The LIS methods of the invention generate exfoliated epithelial cell specimens of the foregut and hindgut.

As is illustrated in the drawings, the invention accordingly is embodied in a method for producing and collecting lavage induced stools for chemical and biological tests of cells exfoliated from a patient's digestive tract, a kit for carrying out the method of the invention, that can be used for home collection procedures, and an advanced formulation of a beverage or beverages, which can also be taken in capsule form. The advanced formulation of beverages can be utilized in conjunction with known test procedures that can be optimized for the given formulations.

A focus of the development of the beverages is the sequencing or step wise administration of lavages, such as to cleanse, and then to exfoliate, and subsequently preserve exfoliated cells to be used in a testing procedure. The pH can also effect the yield of exfoliated cells. A single beverage is simpler for a patient to use and understand, but a cathartic such as bile salts first, followed by a lavage can reduce the requirements for a lavage. For example, a cathartic capsule could be taken first, followed by a lavage. In conjunction with the beverages, the invention further provides for a test kit and method for producing and collecting lavage induced stool for chemical and biological tests of cells exfoliated from a patient's digestive tract. The test kit includes a number of beverages, foods and medications that are to be taken in a specified sequence to cleanse the digestive tract, exfoliate cells therefrom, and subsequently preserve the exfoliated cells to be used in a testing procedure. The invention allows for examination of cells from the whole gut, and for examination of cells from specific targeted areas, such as the colon or stomach, for example.

The test kit can comprise instructions materials, such as written or other types of materials, and typically including a color instruction brochure with a) color pictures of LIS samples in collection containers, b) instructions for the ingestion of foods, beverages, and medications both included with the kit and others, and c) instructions for the proper use of collection and specimen apparatus in the kit. Suitable instruction materials could also readily be provided in other forms, such as video, CD-ROM, and the like. The kit also includes disposable apparatus, including beverage containers, collection pans that fit standard toilet bowl dimensions, collection syringes, a filter device, and a LIS specimen container with fixative (10% buffered formalin) to collect solid and liquid bowel motions generated by the test procedure, mailing carton, labels and gloves. Other disposable apparatus could also be included, such as a funnel, for example. Beverage and medication containers could also be provided, for example, with lines marking water volume to be placed in container for reconstitution of kit beverages and lavage solutions.

The kit also includes the kit beverages, powdered chemicals for reconstitution as beverages or medication, medications, foods, and medicated foods, including sufficient powder to prepare, via reconstitution with water, approximately 6 liters of a sweet tasting balanced electrolyte and salt solution similar to sports drinks. The drink may be modified with additives such as hormnones, proteolytic enzymes, calcium chelating agents such as EDTA, mucolytics, bile salts such as chenodeoxycholate, and buffers such as bicarbonate salts and/or HEPES, which induce increased exfoliation and/or preservation of cells. Hard candies based on sorbitol and/or dextrose can also be provided, to ameliorate the flavor of a final lavage solution. These candies may contain EDTA or other drugs which promote exfoliation of gut mucosa cells. The beverage portion of the kit preferably also includes a cathartic medication, such as 250 ml of magnesium citrate, to induce the production of a formed stool.

Sufficient powder is provided in the kit to prepare up to one liter of a preliminary lavage solution containing buffered mannitol. The solution may contain additives such as hormones, proteolytic enzymes, calcium chelating agents such as EDTA, mucolytics, bile salts such as chenodeoxycholate, and buffers such as bicarbonate salts and/or HEPES, to induce increased exfoliation and/or preservation of cells. Sufficient powder is also provided to prepare up to 4 liters of a final lavage solution containing buffers, inorganic salts, polyethylene glycol, and additives such as hormones, proteolytic enzymes, calcium chelating agents such as EDTA, mucolytics, bile salts such as chenodeoxycholate, and buffers such as bicarbonate salts and/or HEPES, to induce increased exfoliation and/or preservation of cells.

In a presently preferred aspect of the invention, timed release capsules can also be provided, containing substances such as hormones, drugs, buffer salts, proteases, EDTA, or bile salts, which when released into the gut at the proper time in the test procedure improve the yield or preservation of cells recovered in the LIS.

EXAMPLE

After reading the instructions in the instruction brochure, a subject is restricted to ingestion of the provided drink and/or candies while concomitantly ingesting in proper sequence the substances provided by the kit.

Step 1
Initial Cathartic Administration with Feces Collection

Subject takes provided cathartic for preliminary purge with leads to defecation of formed or semi-liquid stool. The first and second bowel motions induced by the cathartic are collected using the apparatus provided by the kit and transferred to two collection containers, one for solid and one for liquid stool. Both are saved for further analysis when the test procedure incorporates analysis of formed stool as an adjunct. Subjects are allowed the electrolyte beverage ad lib during this step until feces collection is finished.

Step 2
Preliminary Lavage Administration

Subject drinks 500 ml of mannitol solution reconstituted according to kit instructions in the provided beverage container. Each stool generated after drinking the mannitol is collected in a pan placed in a standard toilet bowl, and compared to the appearance of the color pictures in the brochure. If an adequate specimen similar to the color picture is produced that is sufficiently free of sediment or formed stool particles, the subject progresses to the next step; otherwise the administration of mannitol is repeated. The pan in the toilet bowl is washed with tap water between defecation, and patients may be allowed water or electrolyte beverage ad lib.

Step 3
Timed Release Capsule Administration

Subject ingests capsules after completing preliminary lavage administration and waits specified time interval, such as approximately two hours, until starting the next step.

Step 4
Final Lavage Administration

Subject ingests 250 mls of final lavage solution every 15 minutes until a sufficiently clear LIS specimen is defecated into the toilet collection pan.

Step 5 Processing of LIS Specimen for Return

Figure 2:
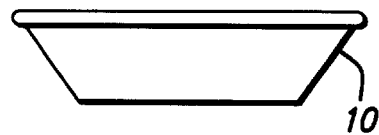
FIG. 2 is a side elevational view of the toilet pan of FIG. 1.
Figure 4:
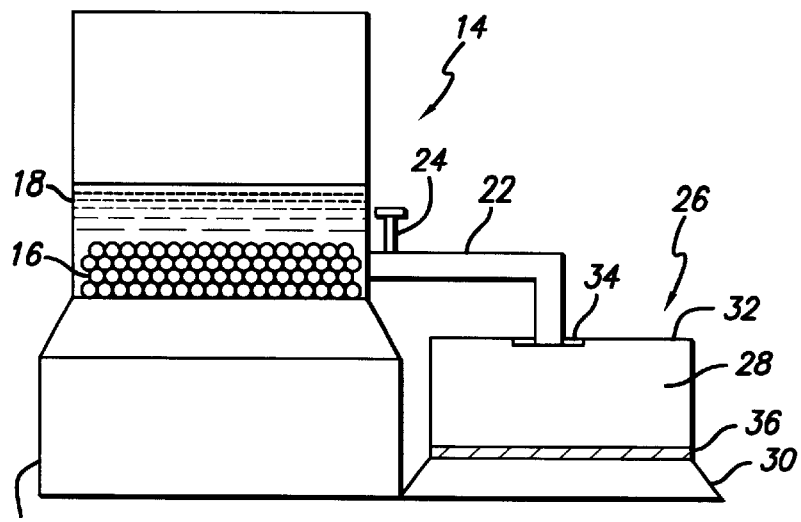
FIG. 4 is a side elevational view of a filtration apparatus and specimen container for use in the method and test kit of the invention.
Figure 3:
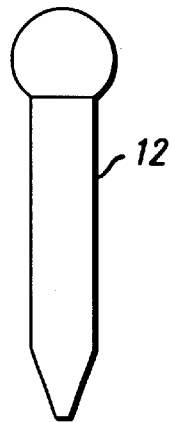
FIG. 3 is a side elevational view of a syringe use in the method and test kit of the invention.

Referring to FIGS. 1 and 2, approximately 50 to 100 ml of the LIS specimen in the toilet pan 10 is transferred via the provided syringe 12 shown in FIG. 3, from the toilet pan into the filtration apparatus 14 illustrated in FIG. 4. The subject then transfers the LIS via the filtration apparatus into a specimen container with fixative. Gloves (not shown) are provided to the subject for safety.

The filtration apparatus preferably contains a coarse filter material 16 such as sand or glass beads, for example, for filtration of the lavage induced stool 18. The filtration apparatus has a base 20, and an outlet 22 with a valve 24 for controlling the transfer of the filtered LIS to a specimen container 26, also shown in FIGS. 4 and 5. The specimen container includes a specimen chamber 28, a base 30, and a lid 32 preferably having a septum 34 with an opening allowing the venting of the specimen container and transfer of the LIS from the outlet of the filtration apparatus. The specimen chamber of the specimen container preferably also contains a fixative 36, such as 10% buffered formalin, for example. Both the specimen container and filter device are specially designed to promote safe and convenient processing of the sample at home with features such as a special seal inside the specimen container to prevent splashing or leakage of fixative during the transfer from the filter device.

Figure 5:
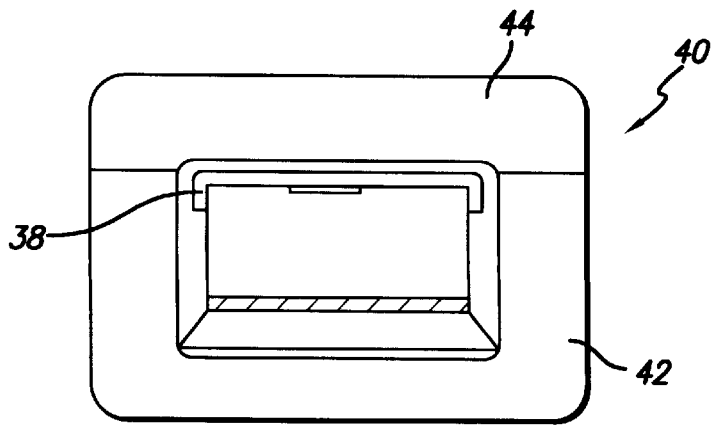
FIG. 5 is a side elevational view of a sealed specimen container and mailing container for use in the method and test kit of the invention.

As is illustrated in FIG. 5, the specimen container also is fitted with a sealing lid 38. After filling the specimen container to the proper level (80 ml) the safety lid is secured and the sealed container is placed in a cushioned mailing carton 40, having a cushioned base 42 and a cushioned lid 44, meeting U.S. biohazard regulations for transport via courier or post to a laboratory for analysis.

While the kit is designed to be used at home for collection of a stool sample induced by the ingestion of a sequence of beverages, medication and medicated foods, it should be readily appreciated that the kit can also be used in an institutional setting, for administration of the beverages of the invention. The kit components and procedures produce stool specimens with preserved exfoliated gastrointestinal cells suitable for medical diagnosis based on histopathologic, biologic, and chemical tests. Cells produced from the kit procedures and components are derived from both the foregut and hindgut allowing diagnosis of both esophageal and rectal cancer as well as other diseases. The kit components and procedures are designed to make the ingested substances palatable and the collection of stool samples convenient and safe.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for producing lavage induced stools for chemical and biological tests of cells exfoliated from a patient's digestive tract including intact cells exfoliated from the upper gut as well as the lower gut in quantities suitable for cytological examination and with sufficient preservation of morphology for the diagnosis of disease, comprising the steps of:

orally administering to a patient at least one preliminary substance selected from the group consisting of an oral cathartic and a lavage solution, to induce bowel motions and to cleanse the patient's digestive tract; and subsequently orally administering to the patient a cell exfoliating lavage solution different from said preliminary substance to increase exfoliation of intact cells from throughout the patient's digestive tract including exfoliating cells from the upper gut as well as the lower gut, said cell exfoliating lavage solution containing a pH buffer to aid in preserving exfoliated cells for medical diagnosis of the patient's digestive tract.

2. The method of claim 1, comprising administering a first lavage solution, followed by orally administering to a patient a final cathartic lavage solution, to minimize the amount of final cathartic lavage solution, compared to single, continuous lavage administration.

3. A method for producing lavage induced stools for chemical and biological tests of cells exfoliated from a patient's digestive tract including intact cells exfoliated from the upper gut as well as the lower gut in quantities suitable for cytological examination and with sufficient preservation of morphology for the diagnosis of disease, comprising the steps of:

orally administering to a patient a first oral cathartic, followed by administering a second oral cathartic; and subsequently orally administering to the patient a cell exfoliating lavage solution to increase exfoliation of intact cells from throughout the patient's digestive tract including exfoliating cells from the upper and lower digestive tract, said cell exfoliating lavage solution containing a pH buffer to aid in preserving exfoliated cells for medical diagnosis of the patient's upper and lower digestive tract.

4. A method for producing lavage induced stools for chemical and biological tests of cells exfoliated from a patient's digestive tract including intact cells exfoliated from the upper gut as well as the lower gut in quantities suitable for cytological examination and with sufficient preservation of morphology for the diagnosis of disease, comprising the steps of:

orally administering to a patient at least one substance selected from the group consisting of an oral cathartic and a lavage solution, to induce bowel motions and to cleanse the patient's digestive tract;

orally administering to the patient at least one exfoliant medication that affects the chemical composition of the induced stool, said exfoliant medication containing a pH buffer to aid in preserving exfoliated cells for medical diagnosis of the patient's upper and lower digestive tract; and orally administering to the patient a cell exfoliating lavage solution to increase exfoliation of intact cells from the patient's upper and lower digestive tract including cells exfoliated from the upper gut as well as the lower gut, said exfoliating lavage solution containing a pH buffer to aid in preserving exfoliated cells for medical diagnosis of the patient's upper and lower digestive tract.

5. A method for producing lavage induced stools for chemical and biological tests of cells exfoliated from a patient's digestive tract including intact cells exfoliated from the upper gut as well as the lower gut in quantities suitable for cytological examination and with sufficient preservation of morphology for the diagnosis of disease, comprising the steps of:

orally administering to a patient a first lavage solution to induce bowel motions and to cleanse the patient's digestive tract;

orally administering to the patient at least one exfoliant medication that affects the chemical composition of the induced stool, said cell exfoliant medication containing a pH buffer to aid in preserving exfoliated cells for medical diagnosis of cancer of the patient's upper and lower digestive tract; and orally administering to the patient a cell exfoliating lavage solution to increase exfoliation of intact cells from the patient's upper digestive tract, said cell exfoliating lavage solution containing a pH buffer to aid in preserving exfoliated cells for medical diagnosis of cancer of the patient's upper and lower digestive tract.

6. A method for producing lavage induced stools for chemical and biological tests of cells exfoliated from a patient's digestive tract including intact cells exfoliated from the upper gut in quantities suitable for cytological examination and with sufficient preservation of morphology for the diagnosis of disease, comprising the steps of:

administering to the patient a first oral cathartic to induce bowel motions;

administering a second oral cathartic to the patient;

orally administering to the patient at least one exfoliant medication that affects the chemical composition of the induced stool, said cell exfoliant medication containing a pH buffer to aid in preserving exfoliated cells for medical diagnosis of cancer of the patient's upper digestive tract; and orally administering to the patient a cell exfoliating lavage solution to increase exfoliation of intact cells from the patient's upper digestive tract, said cell exfoliating lavage solution containing a exfoliating agent selected from the group of inorganic salts, hormones, proteolytic enzymes, calcium chelating agents, EDTA, mucolytics, bile salts, and chenodeoxycholate, to induce increased exfoliation from the patient's upper digestive tract, and containing a pH buffer to aid in preserving exfoliated cells for medical diagnosis of cancer of the patient's upper digestive tract.

7. A method for producing lavage induced stools for chemical and biological tests of cells exfoliated from a patient's digestive tract including intact cells exfoliated from the upper gut in quantities suitable for cytological examination and with sufficient preservation of morphology for the diagnosis of disease, comprising the steps of:

orally administering to a patient an oral cathartic to induce bowel motions;

orally administering to the patient a lavage solution to cleanse the patient's digestive tract; and orally administering to the patient a cell exfoliating lavage solution different from said oral cathartic and said lavage solution to increase exfoliation of intact cells from the patient's upper digestive tract, said cell exfoliating lavage solution containing an exfoliating agent selected from the group of inorganic salts, hormones, proteolytic enzymes, calcium chelating agents, EDTA, mucolytics, bile salts, and chenodeoxycholate, to induce increased exfoliation from the patient's upper digestive tract, and a pH buffer to aid in preserving exfoliated cells for medical diagnosis of cancer of the patient's upper and lower digestive tract.

8. A method for producing lavage induced stools for chemical and biological tests of cells exfoliated from a patient's digestive tract including intact cells exfoliated from the upper gut as well as the lower gut in quantities suitable for cytological examination and with sufficient preservation of morphology for the diagnosis of disease, comprising the steps of:

orally administering to a patient an oral cathartic to induce bowel motions;

orally administering to the patient a lavage solution to cleanse the patient's digestive tract;

orally administering to the patient at least one exfoliant medication that affects the chemical composition of the induced stool, said cell exfoliant medication containing an exfoliating agent selected from the group of inorganic salts, hormones, proteolytic enzymes, calcium chelating agents, EDTA, mucolytics, bile salts, and chenodeoxycholate, to induce increased exfoliation of intact cells from the patient's upper and lower digestive tract; and orally administering to the patient a cell exfoliating lavage solution to increase exfoliation of intact cells from the patient's upper digestive tract, said cell exfoliating lavage solution containing a pH buffer to aid in preserving exfoliated cells for medical diagnosis of cancer of the patient's upper and lower digestive tract.

9. A method for producing lavage induced stools for chemical and biological tests of cells exfoliated from a patient's digestive tract including intact cells exfoliated from the upper gut as well as the lower gut in quantities suitable for cytological examination and with sufficient preservation of morphology for the diagnosis, of disease, comprising the steps of:

orally administering to a patient an oral cathartic to induce bowel motions and to cleanse the patient's digestive tract; and subsequently orally administering to the patient a cell exfoliating lavage solution different from said preliminary substance to increase exfoliation of intact cells from throughout the patient's digestive tract including intact cells exfoliated from the upper gut as well as lower gut, said cell exfoliating lavage solution containing an exfoliating agent to induce increased exfoliation from the patient's upper and lower digestive tract and a pH buffer to aid in preserving exfoliated cells for medical diagnosis of the patient's upper and lower digestive tract, said exfoliating agent being selected from the group of inorganic salts, hormones, proteolytic enzymes, calcium chelating agents, EDTA, mucolytics, bile salts, and chenodeoxycholate.

10. A method for producing lavage induced stools for chemical and biological tests of cells exfoliated from a patient's digestive tract including intact cells exfoliated from the upper gut as well as the lower gut in quantities suitable for cytological examination and with sufficient preservation of morphology for the diagnosis of disease, comprising the steps of:

orally administering to a patient an oral cathartic to induce bowel motions and to cleanse the patient's digestive tract;

orally administering to the patient at least one exfoliant medication that affects the chemical composition of the induced stool, said cell exfoliant medication containing an exfoliating agent selected form the group of inorganic salts, hormones, proteolytic enzymes, calcium chelating agents, EDTA, mucolytics, bile salts, and chenodeoxycholate, to induce increased exfoliation from the patient's upper and lower digestive tract; and subsequently orally administering to the patient cell exfoliating lavage solution different from said preliminary substance to increase exfoliation of intact cells from throughout the patient's digestive tract including intact cells exfoliated from the upper gut as well as lower gut, said cell exfoliating lavage solution containing a pH buffer to aid in preserving exfoliated cells for medical diagnosis of the patient's upper and lower digestive tract.

* * * * *